(12) United States Patent
Brown et al.

(10) Patent No.: US 7,767,682 B2
(45) Date of Patent: Aug. 3, 2010

(54) MEDICAMENTS

(75) Inventors: Kathleen Keating Brown, Durham, NC (US); Bonnie Blazer-Yost, Indianapolis, IN (US)

(73) Assignee: GlaxoSmithKline LLC, Philadelphia, PA (US)

( * ) Notice: Subject to any disclaimer, the term of this patent is extended or adjusted under 35 U.S.C. 154(b) by 306 days.

(21) Appl. No.: 11/817,523

(22) PCT Filed: Mar. 1, 2006

(86) PCT No.: PCT/US2006/007189

§ 371 (c)(1),
(2), (4) Date: Aug. 31, 2007

(87) PCT Pub. No.: WO2006/096398

PCT Pub. Date: Sep. 14, 2006

(65) Prior Publication Data

US 2008/0113996 A1    May 15, 2008

Related U.S. Application Data

(60) Provisional application No. 60/658,255, filed on Mar. 3, 2005.

(51) Int. Cl.
*A61K 31/497* (2006.01)
*A61K 31/4439* (2006.01)
*A61P 13/12* (2006.01)

(52) U.S. Cl. .................. 514/254.02; 514/342

(58) Field of Classification Search .............. None
See application file for complete search history.

(56) References Cited

U.S. PATENT DOCUMENTS

| | | |
|---|---|---|
| 6,765,013 B2 | 7/2004 | Pfahl et al. |
| 6,974,826 B2 | 12/2005 | Pfahl et al. |
| 2003/0045553 A1* | 3/2003 | Bussolari et al. ............ 514/340 |
| 2004/0127443 A1* | 7/2004 | Pershadsingh ............... 514/44 |

FOREIGN PATENT DOCUMENTS

| | | |
|---|---|---|
| EP | 1277729 A1 | 1/2003 |
| WO | 9521608 A1 | 8/1995 |
| WO | 2005041872 A2 | 5/2005 |

OTHER PUBLICATIONS

Vippagunta (Adv. Drug Del. Rev., 2001, vol. 48, 2001, pp. 3-26.*
Muto et al.; "Pioglitazone Improves the Phenotype and Molecular Defects of a Targeted Pkd1 Mutant"; Human Molecular Genetics; 2002; vol. 11, No. 15; pp. 1731-1742.
Ohga et al.; "Thiazolidinedione Ameliorates Renal Injuries through Anti-Inflammatory Actions by Inhibition of NF-κB Activation in Experimental Diabetic Rats"; Diabetologia; 2004; vol. 47, Suppl. 1; p. A398, Abstract No. 1112.
Sivarajah et al.; "Agonists of Peroxisome-Proliferator Activated Receptor-Gamma Reduce Renal Ischemia/ Reperfusion Injury"; American Journal of Nephrology; 2003; vol. 23; pp. 267-276.
Supplementary EP Search Report dated Apr. 7, 2008 corresponding to EP Application No. 06736499.

* cited by examiner

*Primary Examiner*—Brian-Yong S Kwon
(74) *Attorney, Agent, or Firm*—Robert H. Brink (57) ABSTRACT

Methods of prevention or treatment of renal diseases or conditions associated with abnormal ion flux, in particular autosomal dominant polycystic kidney disease, with a modulator of human peroxisome proliferator activated receptor gamma.

1 Claim, 4 Drawing Sheets

MEDICAMENTS

CROSS-REFERENCE TO RELATED APPLICATIONS

This application is filed pursuant to 35 U.S.C. §371 as a United States National Phase Application of International Application No. PCT/US2006/007189 filed Mar. 1, 2006, which claims priority from U.S. Provisional Application No. 60/658,255 filed Mar. 3, 2005.

FIELD OF THE INVENTION

The present invention is concerned with methods of treatment, pharmaceutical compositions and medicaments for use in treatment. More particularly, the invention relates to modulators of Peroxisome Proliferator Activated Receptor gamma (PPARgamma). In another aspect, the present invention relates to methods for prevention or treatment of renal diseases or conditions associated with abnormal ion flux including autosomal dominant polycystic kidney disease (ADPKD).

BACKGROUND OF THE INVENTION

Perixome Proliferator Activated Receptors (PPARs) are orphan receptors belonging to the steroid/retinoid receptor superfamily of ligand-activated transcription factors. See, for example Willson T. M. and Whali, W., Curr. Opin. Chem. Biol., 1, pp 235-241 (1997) and Willson T. M. et. Al., J. Med. Chem., 43, P527-549 (2000). The binding of agonist ligands to the receptor results in changes in the expression level of mRNAs encoded by PPAR target genes.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signalling cascade and lipid homeostasis (H. Keller and W. Wahli, Trends Endocrinol. Metab. 291-296, 4 (1993)).

It has been reported that the thiazolidinedione class of compounds including rosiglitazone and pioglitazone are potent and selective activators of PPAR-gamma and bind directly to the PPAR-gamma receptor (J. M. Lehmann et al., J. Biol. Chem. 12953-12956, 270 (1995)), providing evidence that PPAR-gamma is a possible target for the therapeutic actions of the thiazolidinediones. Since this observation, activation of this nuclear hormone receptor has been shown to have pleiotropic metabolic and nonhypoglycemic effects. Clinical use of the agents in the treatment of Type 2 diabetes mellitus (or non insulin dependent diabetes mellitus (NIDDM)) is associated with sensitization to the glucose lowering effects of insulin as well as potentiation of other biological actions of insulin in target tissues. When used as monotherapy, there are reports of fluid retention resulting in volume expansion and, in some patients, clinical edema. The incidence of edema appears to be increased when both these agents are used in combination with insulin (Nesto R. W. et al, 2003, Circulation, 108, 2941-2948). However, the mechanisms involved in these effects have not been well described but the nature of the presentation suggests an integrated physiological response which includes an effect on renal salt and water balance. PPAR gamma receptors have been found in the renal collecting duct (Guan Y. et al; 2001, Kidney Int. 60, 14-30) and, therefore, the PPAR gamma agonists might be involved directly in renal tubular metabolism or could have secondary effects on salt and water homeostasis.

Autosomal-dominant polycystic kidney disease (ADPKD) is one of the most prevalent single gene disorders to affect humans with an incidence of approximately 1 in 1000 live births in all ethnic groups (Gabow P. A., 1993, N. Engl. J. Med. 329: 332-342). The disease is caused by mutations in the polycystin proteins that initiate a cascade of events resulting in the formation of multiple fluid-filled epithelial cysts which progressively destroys the architecture of the kidney leading to severe renal failure. Currently, no therapies exist for ADPKD which account for 8-10% of patients requiring kidney transplantation or dialysis (Gabow P. A., 1993, N. Engl. J. Med. 329: 332-342). It will therefore be appreciated that it is desirable to identify and develop treatments for this disease.

The development and growth of ADPKD cysts involve the proliferation of immature epithelial cells, changes in the extracellular matrix and the accumulation of fluid in the cyst cavity. This is driven by CAMP stimulated cell proliferation and Cl-secretion via the cystic fibrosis transmembrane conductance regulator (CFTR) Cl-channel. Thus it is thought that inhibitors at the CFTR Cl-channel may retard cyst growth principally by blocking fluid accumulation within the cyst lumen. (Hongyu Li et al., 2004, Kidney International 66; 1926-1938).

The present inventors have found that modulators of the peroxisome proliferator activated receptor gamma (PPAR gamma) may inhibit anion secretion via CFTR in renal cells and thus are of potential therapeutic benfeit in the treatment of renal diseases or conditions associated with abnormal ion flux, including ADPKD.

SUMMARY OF THE INVENTION

In one aspect, the invention provides a compound which is a modulator of human PPAR gamma (hPPAR gamma) or a pharmaceutically acceptable salt or solvate thereof for use in the treatment of renal diseases or conditions associated with abnormal ion flux.

In a further aspect there is provided a pharmaceutical composition comprising a hPPAR gamma modulator or a pharmaceutically acceptable salt or solvate thereof for use in the treatment of renal diseases or conditions associated with abnormal ion flux.

In a further aspect the invention provides a method of treating renal diseases or conditions associated with abnormal ion flux comprising administering hPPAR gamma modulator or a pharmaceutically acceptable salt or solvate thereof.

In a further aspect, the invention provides the use of a hPPAR gamma modulator or a pharmaceutically acceptable salt or solvate thereof in the manufacture of a medicament for treating renal diseases or conditions associated with abnormal ion flux.

DESCRIPTION OF THE FIGURES

FIG. 1:
Ion transport response of MDCK-C7 cells (short circuit current) to stimulation by ADH in control and amiloride-pretreated cells. The entire time-course is shown in FIG. 1A and the first 10 minutes shown in FIG. 1B.

FIG. 3:

Time course of the ion transport response of MDCK-C7 cells to stimulation by ADH in cells pre-treated for 18 hours with GI262570X. Ion transport is measured as short-circuit current (SCC). A positive deflection indicates cation movement from apical to serosal bathing medium or anion movement from serosal to apical medium.

FIG. 4:

Ion transport response of MDCK-C7 cells to stimulation by ADH in cells pretreated for 18 hours with GI262570X. Ion transport is measured as short-circuit current (SCC). The data are shown as the initial 4 minutes of the response. A positive deflection indicates cation movement from apical to serosal bathing medium or anion movement from serosal to apical medium.

DETAILED DESCRIPTION OF THE INVENTION

As used herein the term "hPPAR gamma modulator" is meant a compound which alters the activity of the hPPAR gamma receptor either directly (by binding thereto and altering activity) or indirectly (for example, by causing some change in receptor expression and/or degradation rate) thus increasing or decreasing the transcription of PPAR-responsive genes relative to the PPAR receptor in a basal state— either unliganed in an in vitro setting or in an in vitro setting, in the presence of "normal" amounts of endogenous PPAR ligands. This definition thus embraces agonists, partial agonists, antagonists, partial antagonists.

The hPPAR gamma agonists of formula (I) may be agonists or partial agonists of only gamma ("selective agonists"), agonists or partial agonists for two PPAR subtypes including gamma ("dual agonists"), or agonists or partial agonists for all three subtypes ("pan agonists").

In one aspect the hPPAR gamma modulators are human (h) PPAR gamma agonists. In a further aspect they are also agonists of at least one of hPPARα or hPPARδ (dual agonists). In one aspect they are pan hPPAR agonists.

In a further aspect, the hPPAR gamma modulators are hPPAR gamma agonists or partial agonists.

As used herein, by "agonists", or "activating compound", or "activator", or the like, is meant those compounds which have a pKi of at least 5.0 preferably at least 6.0 to the relevant PPAR, for example hPPAR gamma in the binding assay described for example in WO 02/059098 (or similar assays), and which achieve at greater than 70% activation of the relevant PPAR relative to the appropriate indicated positive control in the transfection assay described in WO02/059098 (or similar assays) at concentrations of $10^{-5}$M or less. More preferably, the compounds of this invention achieve greater than 70% activation of at least on human PPAR in the relevant transfection assay at concentrations of $1^{-5}$M or less. More preferably the compounds of the invention achieve greater than 70% activation of at least on human PPAR in the relevant transfection assay at concentrations of $1^{-7}$M or less.

Partial agonists can be defined as compounds that transactivate the relevant hPPAR, for example hPPAR alpha in CV1 cells with less than 70%, typically less than 50% fold activation compared to the reference PPAR full agonist in the transfection assays of the type described in WO 97/31907. A compound having activity at more than on hPPAR may independently demonstrate full or partial agonist activity at each hPPAR.

The term "treatment" as used herein includes prophylaxis as well as alleviation of established diseases or conditions. The PPAR gamma modulators may be used as compounds or salts or solvates thereof.

In one aspect the renal disease or condition associated with abnormal ion flux is ADPKD.

In one aspect the PPAR gamma modulator is described in European Patent 306228. This describes a class of PPAR gamma agonists which are thiazolidinedione derivatives for use as insulin sensitisers in the treatment of Type 2 diabetes mellitus. These compounds have anti-hyperglycaemic activity. One preferred compound described therein is known by the chemical name 5-[4-[2-(N-methyl-N-(2-pyridyl)amino) ethoxy]benzyl]thiazolidine-2,4-dione and has been given the generic name rosiglitazone. Salts of this compound including the maleate salt are described in WO94/05659. European Patent Applications, Publication Numbers: 0008203, 0139421, 0032128, 0428312, 0489663, 0155845, 0257781, 0208420, 0177353, 0319189, 0332331, 0332332, 0528734, 0508740; International Patent Application, Publication Numbers 92/18501, 93/02079, 93/22445 and U.S. Pat. Nos. 5,104,888 and 5,478,852, also disclose certain thiazolidinedione insulin sensitisers. Specific compounds that may be mentioned include 5-[4-[2-(5-ethyl-2-pyridyl)ethoxy]benzyl] thiazolidine-2,4-dione (also known as pioglitazone), 5-[4-[(1methylcyclohexyl)methoxy]benzyl]thiazolidine-2,4-dione (also known as ciglitazone), 5[[4-[(3,4-dihydro-6-hydroxy-2,5,7,8-tetramethyl-2H-1-benzopyran-2-yl) methoxy]phenyl]methyl]-2,4-thiazolidinedione (also known as troglitazone) and 5-[(2-benzyl-2,3-dihydrobenzopyran)-5-ylmethyl)thiazolidine-2,4-dione (also known as englitazone).

U.S. Pat. No. 6,294,580 (the disclosure of which is herein incorporated by reference in its entirety) describes a series of PPAR gamma agonist compounds not of the thiazolidinedione class but which are instead 0- and N- substituted derivatives of tyrosine which nevertheless are effective as insulin sensitisers in the treatment of Type 2 diabetes mellitus. One such compound has chemical name N-(2-benzoylphenyl)-O-[2-(5-methyl-2-phenyl-4-oxazolyl)ethyl]-L -tyrosine (also known as 2(S)-(2-benzoyl-phenylamino}-3-{4-[2-5-methyl-2-phenyl-oxazol-4-yl)-ethoxy]phenyl}-propionic acid, or by the generic name farglitazar, or GI262570. A method of synthesising farglitazar is shown in Example 29.

Further compounds are described in WO 02/062774, WO 02/30895, WO 00/08002, WO 02/059098, WO 03/074495.

In a preferred embodiment the compound is farglitazar (particularly the sodium salt), rosiglitazone (particularly the maleate salt), 2-({4-[({4-({4-[4-(ethyloxy)phenyl]-1-piperazinyl}methyl)-2-[4-(trifluoromethyl)phenyl]-1,3-thiazol-5-yl}methyl)thio]phenyl}oxy)-2-methylpropanoic acid:

(for preparation of this compound, see WO 02/059098), ({2-ethyl-4-[({4-({4-[4-(methyloxy)phenyl]-1-piperazinyl}methyl)-2-[4-(trifluoromethyl)phenyl]-1,3-thiazol-5-yl}methyl)thio]phenyl}oxy)acetic acid:

(for preparation of this compound, see WO 02/059098),
2-{4-[{2-[2-fluoro-4-(trifluoromethyl)phenyl]-4-methyl-1,3-thiazol-5-yl}methyl)sulfanyl]-2-methylphenoxy}-2-methylpropanoic acid (for preparation of this compound, see WO 02/062774).

Where stereocenters exist in compounds which are PPAR modulators, the present invention includes the use of all possible stereoisomers and geometric isomers of such compounds and includes not only racemic compounds but also the optically active isomers as well. When a compound is desired as a single enantiomer, it may be obtained either by resolution of the final product or by stereospecific synthesis from either isomerically pure starting material or any convenient intermediate. Resolution of the final product, an intermediate or a starting material may be affected by any suitable method known in the art. See, for example, Stereochemistry of Carbon Compounds by E. L. Eliel (Mcgraw Hill, 1962) and Tables of Resolving Agents by S. H. Wilen. Additionally, in situations where tautomers of the compounds are possible, the present invention is intended to include the use of all tautomeric forms of the compounds.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "physiologically functional derivative" refers to any pharmaceutically acceptable derivative of a PPAR gamma modulator, for example, an ester or an amide, which upon administration to a mammal is capable of providing (directly or indirectly) said PPAR gamma modulator or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is incorporated herein by reference to the extent that it teaches physiologically functional derivatives.

As used herein, the term "solvate" refers to a complex of variable stoichiometry formed by a solute of a PPAR gamma modulator (or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid.

It will be appreciated by those skilled in the art that the PPAR gamma modulator may also be utilized in the form of a pharmaceutically acceptable salt or solvate thereof in the methods of the present invention. Suitable pharmaceutically acceptable salts can include acid or base addition salts.

A pharmaceutically acceptable acid addition salt can be formed by reaction of a compound with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt can comprise or be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

A pharmaceutically acceptable base addition salt can be formed by reaction of a compound with a suitable inorganic or organic base (e.g. triethylamine, ethanolamine, triethanolamine, choline, arginine, lysine or histidine), optionally in a suitable solvent such as an organic solvent, to give the base addition salt which is usually isolated for example by crystallisation and filtration.

Other suitable pharmaceutically acceptable salts include pharmaceutically acceptable metal salts, for example pharmaceutically acceptable alkali-metal or alkaline-earth-metal salts such as sodium, potassium, calcium or magnesium salts; in particular pharmaceutically acceptable metal salts of one or more carboxylic acid moieties that may be present in he compound.

Other non-pharmaceutically acceptable salts, eg. oxalates, may be used, for example in the isolation of compounds of the invention, and are included within the scope of this invention.

The invention includes within its scope the use of all possible stoichiometric and non-stoichiometric forms of the salts of the compound.

References hereinafter to a PPAR gamma modulator include both compounds and their pharmaceutically acceptable salts and solvates.

The PPAR gamma modulators and their pharmaceutically acceptable salts and solvates are conveniently administered in the form of pharmaceutical compositions. Such compositions may conveniently be presented for use in conventional manner in admixture with one or more physiologically acceptable carriers or excipients. The carrier(s) must be "acceptable" in the sense of being compatible with the other ingredients of the formulation and not deleterious to the recipient thereof.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt, and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts and solvates thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists, which may be generated by means of various types of metered, dose pressurised aerosols, nebulizers or insufflators.

Pharmaceutical compositions adapted for vaginal administration may be presented as pessaries, tampons, creams, gels, pastes, foams or spray compositions.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of composition in question, for example those suitable for oral administration may include flavouring agents.

A therapeutically effective amount of a compound of the present invention will depend upon a number of factors including, for example, the age and weight of the animal, the precise condition requiring treatment and its severity, the nature of the composition, and the route of administration, and will ultimately be at the discretion of the attendant physician or veterinarian. However, an effective amount of a compound of formula (I) for the treatment of renal diseases or conditions associated with abnormal ion flux, including ADPKD, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. When the PPAR modulator is farglitazar, dosages of 2 to 10 mg per day are envisaged. An effective amount of a salt or solvate, may be determined as a proportion of the effective amount of the compound per se. Pharmaceutical compositions may be presented in unit dose forms containing a predetermined amount of active ingredient per unit dose. Conveniently, unit dosage compositions are those containing a daily dose or sub dose or an appropriate fractions thereof of the active ingredient.

The PPAR gamma modulator for use in the instant invention and salts and solvates thereof may be used in combination with one or more other therapeutic agents. The invention thus provides in a further aspect the use of a combination comprising a PPAR gamma modulator and salts and solvates thereof with a further therapeutic agent or agents for use in the prevention or treatment of renal diseases or conditions associated with abnormal ion flux.

When the PPAR gamma modulators are used in combination with other therapeutic agents, the compounds may be administered either sequentially or simultaneously by any convenient route.

The combinations referred to above may conveniently be presented for use in the form of a pharmaceutical composition and thus pharmaceutical compositions comprising a combination as defined above optimally together with a pharmaceutically acceptable carrier or excipient comprise a further aspect of the invention. The individual components of such combinations may be administered either sequentially or simultaneously in separate or combined pharmaceutical compositions.

When combined in the same composition it will be appreciated that the two compounds must be stable and compatible with each other and the other components of the composition. When formulated separately they may be provided in any convenient composition, conveniently in such a manner as are known for such compounds in the art.

When a PPAR gamma modulator is used in combination with a second therapeutic agent active against the same disease, the dose of each compound may differ from that when the compound is used alone. Appropriate doses will be readily appreciated by those skilled in the art.

The following examples are set forth to illustrate the present invention. Accordingly, the following Example section is in no way intended to limit the scope of the invention contemplated herein.

EXAMPLES

In the kidney, the specific portions of the nephron in which PPAR gamma is expressed include glomerular mesangial cells, renal inner medullary collecting duct cells and renal medullary interstitial cells (Yang et al, 1999, Am. J. Physiol. 277, F966-F973). Studying the direct renal functional effects of these agents, in the absence of the systemic effects on blood pressure and vascular resistance, requires an in vitro system with the characteristics and hormonal responsiveness of the principle cells of the distal nephron. $Na^+$ and fluid balance are regulated by the principal cell type of the distal convoluted tubule and cortical collecting duct under the control of numerous steroid and peptide hormones including aldosterone, insulin, vasopressin, and insulin-like growth factor.

The Madin-Darby canine kidney (MDCK) cell line expresses many characteristics of the renal collecting duct.

The MDCK-C7 subclone forms a high-resistance, hormone-responsive model of the principal cells, which are found in distal sections of the renal tubule. The electrophysiological technique of short-circuit current measurement has been used to examine the response to antidiuretic hormone (ADH) in the MDCK-C7 clone. Three temporally discrete electrogenic ion transport phenomena have been described and characterized in these cells (Blazer-Yost et al, 1996; Lahr et al, 2000). Initially, the cells exhibit anion secretion through the cystic fibrosis transmembrane conductance regulator (CFTR). The presence of CFTR was confirmed by immunoprecipitation followed by Western blotting. The CFTR-mediated anion secretion is transient and is followed, in time, by a verapamil- and $Ba^{2+}$-sensitive anion secretion or cation absorption and, finally, by $Na^+$ reabsorption via epithelial $Na^+$ channels (ENaC). The characterization of the various ion transport phenomena substantiates this cell line as a model renal epithelium that can be used to study the hormonal and metabolic regulation of ion transport as well as the ability of pharmacological agents to affect ion transport.

Materials

The hormones and inhibitors used in these experiments were: ADH ([arg]-vasopressin, Sigma, St. Louis, Mo.); amiloride hydrochloride (Sigma); NPPB (Biomol Research, Plymouth Meeting, Pa.), Verapamil hydrochloride (ICN Biomedical, Aurora, Ohio). GI262570X (Farglitazar) was provided by GlaxoSmithKline Medicinal Chemistry and may be prepared as described in U.S. Pat. No. 6,294,580.

Methods

MDCK-C7 Cell Culture:

The MDCK-C7 cells were grown in a 37° C. humidified incubator with a 5% CO2 and 95% O2 gas mixture. Initially the cells were grown in 75 cm² flasks and fed with Minimal Media with Earle's salts, non-essential amino acids and L-glutamine (MEM; Gibco/BRL, Grand Island, N.Y., USA) supplemented with 10% fetal bovine serum (Sigma), 26 mM $NaHCO_3$ and adjusted to pH 7.0. The confluent cells were subcultured by trypsinization and the cells were seeded (5.4× $10^4$ cell/cm²) onto Nucleopore polycarbonate membranes forming the bottom of Transwell chambers (Costar, Cambridge, Mass., USA). The Transwell chambers were placed in specially designed tissue culture plates to form a two compartment system in which media are added to both apical and basolateral surfaces. The media were aspirated and replaced three times per week. The cells were used between passages 73 and 96.

Experimental Protocols

Electrophysiological Studies:

Nucleopore filters (4.7 cm²) containing confluent MDCK-C7 cells (10-16 days) were removed from the Transwell chambers and clamped between the halves of an Ussing chamber (World Precision Instruments, Sarasota, Fla.). Each half of the chamber contained a tapered fluid compartment with openings for voltage electrodes (close to the epithelial membrane) and current electrodes (at the opposite end of the chamber). The fluid chamber was water jacketed to maintain constant temperature (37° C.). The cells were bathed in serum-free MEM. The media were circulated in the chambers by means of a 5%$CO2/O_2$ gas lift. The electrodes were connected to a voltage-clamp amplifier (Current Voltage Clamp; World Precision Instruments) for measurement of net ion flux as monitored under short-circuit conditions (SCC; short circuit current) [Ussing, 1951]. Transepithelial resistance was calculated by applying a 2-mV pulse across the epithelium and measuring the resultant deflection in SCC. Data from cultures were used only if they maintained a resistance >1000 W cm². Transepithelial resistance (an indication of cellular viability) was monitored throughout the entire duration of each electrophysiological experiment by pulsing the tissues with a 2000 μV pulse every 200 seconds. Resistance values were calculated from the resulting current deflections using Ohm's law.

The cultures were placed in the Ussing chambers and incubated under short-circuited conditions until a steady baseline transport was achieved (0.5-1 h). In the experiments to characterize the ADH-induced ion transport phenomena, the cultures were pre-incubated with the inhibitors 30 minutes prior to the addition of ADH. In the experiments with GI262570X, compound was added 18 hrs. prior to the addition of ADH. ADH was added to the serosal bathing media; amiloride was added to the apical media 30 min after ADH to determine the portion of the transport due to flux through the amiloride-sensitive $Na^+$ channel. The concentrations of effectors used were: ADH, 0.1 IU/ml; amiloride, 30 μM; NPPB, 500 μM; verapamil, 25 μM, and GI262570X (concentration range from 1 nM -1 μM). Each experiment was performed using matched cultures grown in parallel. The data are presented as means±SE with n indicating the number of different experiments.

Results

Figure 1A:
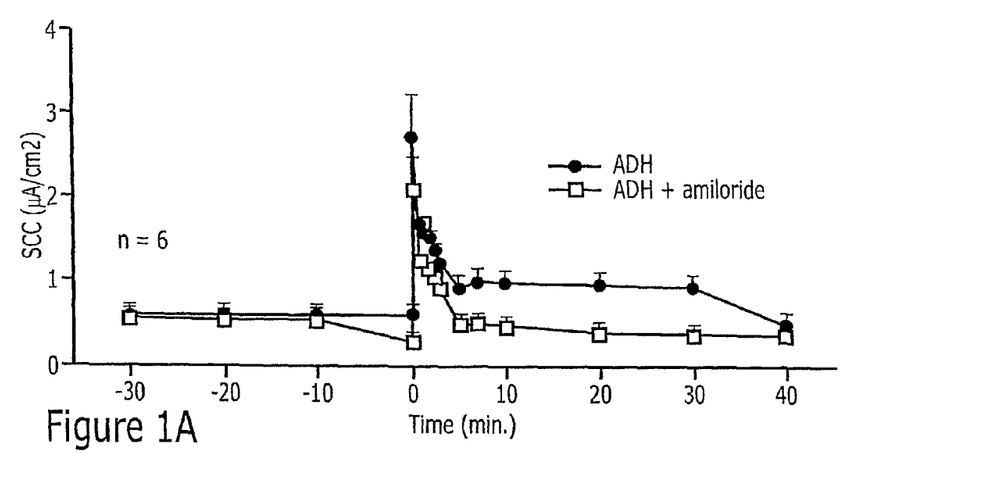
Figure 1B:
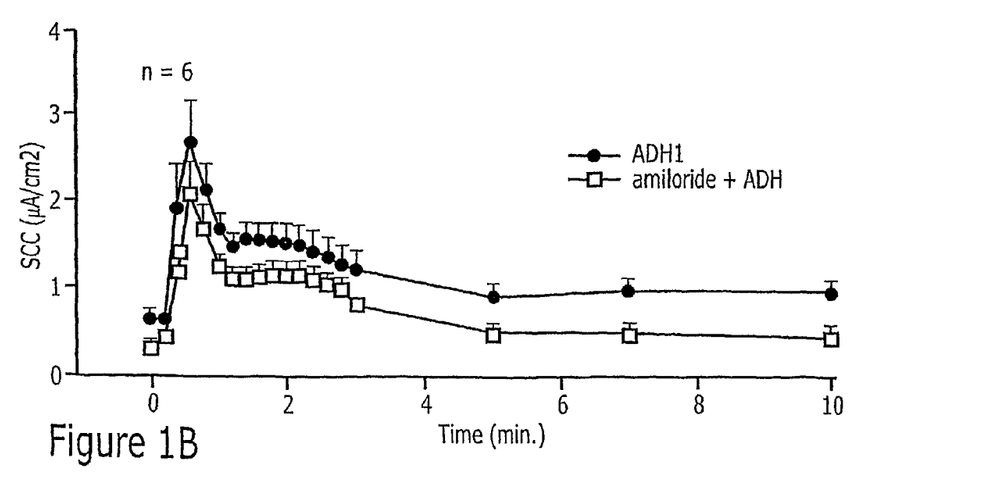
Figure 2A:
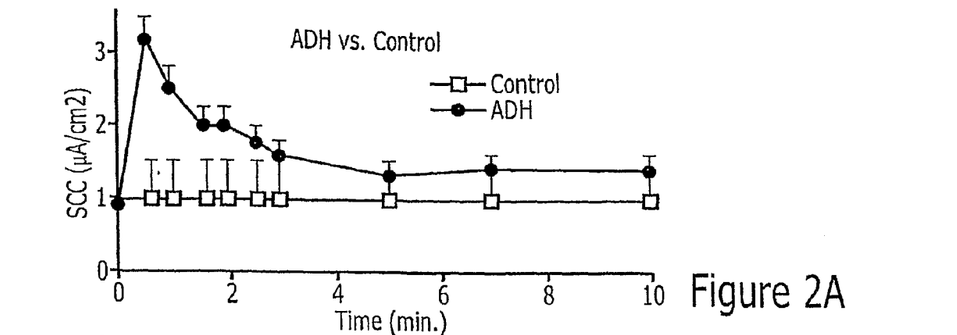
FIG. 2:
Ion transport response of MDCK-C7 cells to stimulation by ADH in cells pretreated with inhibitors of CFTR. Ion transport is measured as short-circuit current (SCC). A positive deflection indicates cation movement from apical to serosal bathing medium or anion movement from serosal to apical medium.
Figure 2B:
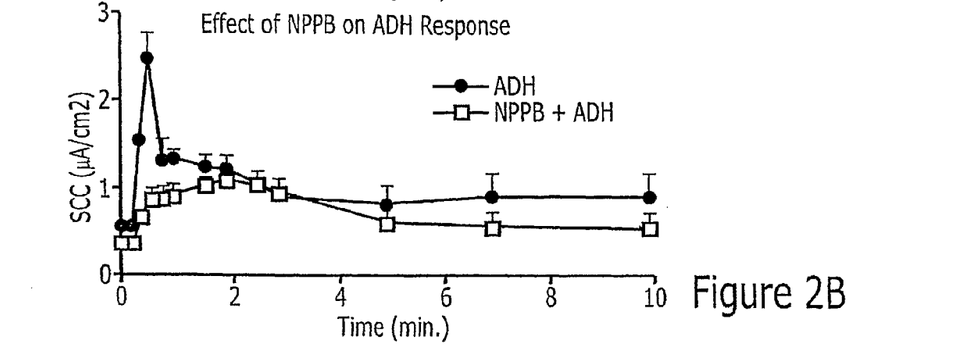
Figure 2C:
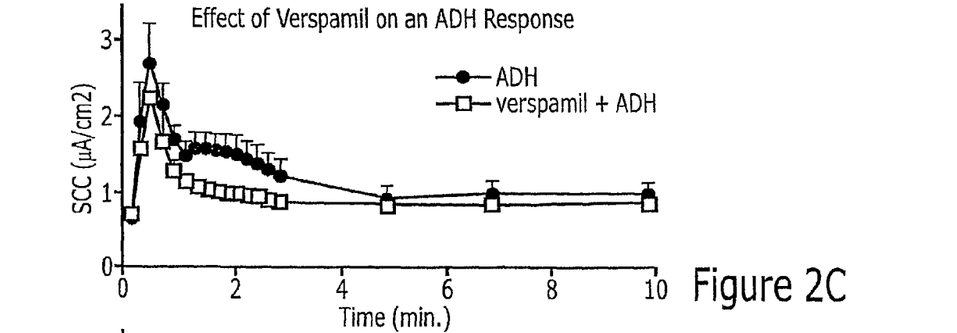
Figure 2D:
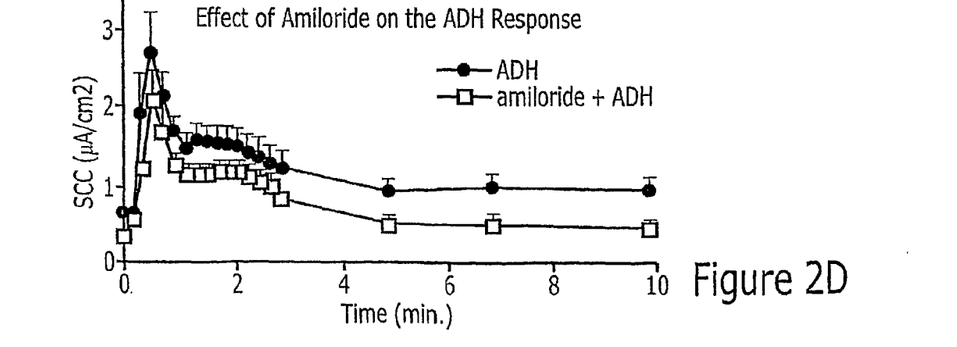

The measurement of short circuit current can be used to assess ion transport across monolayers of renal cells in culture. By convention, a positive deflection indicates cation movement from the apical to serosal bathing medium (reabsorption) or anion movement from serosal to apical membrane (secretion). Stimulation of MDCK-C7 cells with [arg]-vasopressin (ADH, 100 mU/ml) results in a multiphasic response in which there is a rapid increase in short circuit current (FIGS. 1A and B) composed of both an immediate peak of ion transport within 1 minute (FIG. 1B) followed by a more sustained maximum response over the next 2-5 minutes and a later sustained response which subsequently declines toward a pre-treatment baseline over the next 30 minutes. The later sustained responses have been shown to represent transport through the epithelial $Na^+$ channel (ENaC). However, amiloride only blocks the later sustained SCC response suggesting that the earlier response to ADH represented events mediated by other transporters.

The identity of the ion channels and transporters involved in the complex response produced by ADH has been characterized pharmacologically through the use of inhibitors as shown in FIG. 2. In panel A, the SCC response in cells treated with ADH alone is multiphasic compared to untreated cells which manifest only a small sustained increase in SCC of approximately 1 μA/cm² in the absence of ADH. In panel B, NPPB (500 μM), a non-specific inhibitor of the cystic fibrosis transmembrane conductance regulator CFTR was added to the apical bathing medium and is shown to significantly diminish the rapid transient ion transport response to ADH. There is a portion of the ion flux response to ADH that is amiloride- and NPPB-insensitive and is blocked by verapamil (Panel C), an inhibitor of L-type $Ca^{2+}$ as well as a modulator of the inositol-1,4,5,-triphosphate receptor thus suggesting a role for intracellular $Ca^{2+}$ in the response. Panel D shows the effects of amiloride to decrease the later sustained ion transport response.

Figure 3:
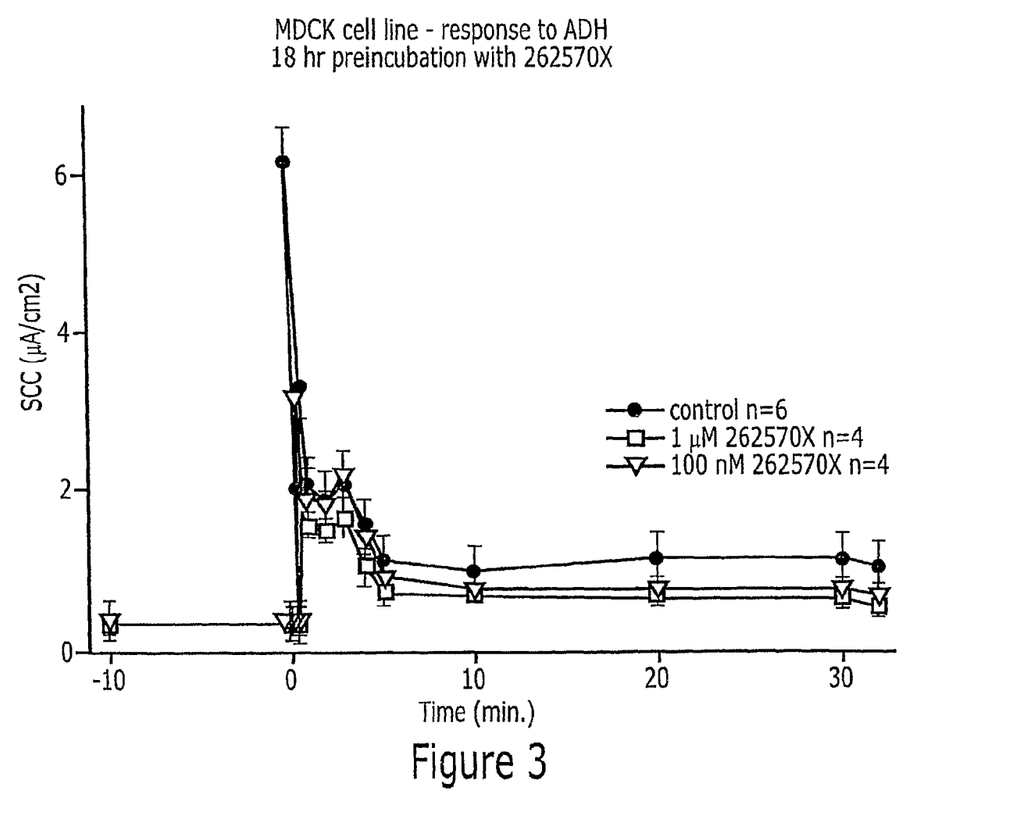
Figure 4:
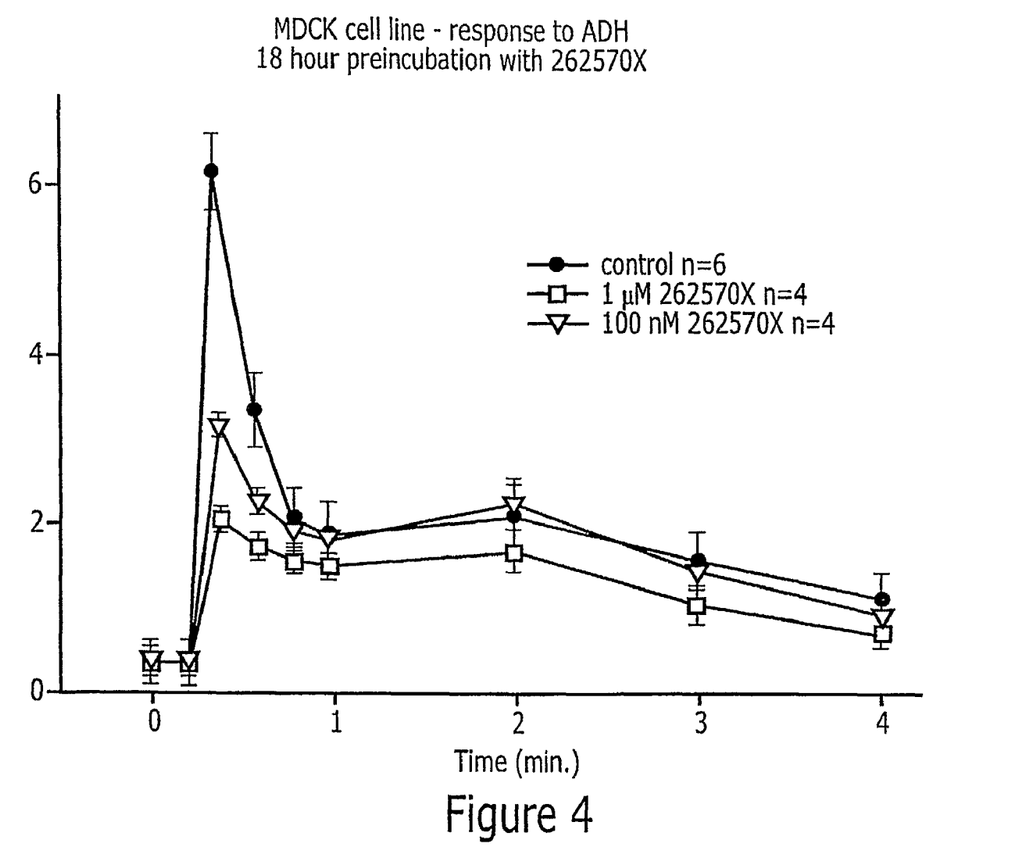

The effects of GI262570X, are graphically depicted in FIGS. 3 and 4. The complete 30 minutes time-course of the ADH-induced ion transport response as well as the baseline stabilization period is depicted in FIG. 3 and the expanded early rapid transient response over the first 4 minutes is shown in FIG. 4. In these experiments the cells were pre-incubated with GI262570X for 18 hrs prior to exposure to ADH. There was no compound-related effect on the baseline SCC (−10 to 0 minutes). However, comparison of the magnitude of the multiphasic SCC response to in cells exposed to ADH±GI262570X (100 nM or 1 μM, n=4/dose and n=6 controls) shows that the initial rapid transient response in significantly attenuated by both 100 nM ($p<0.05$) and 1 μM ($p<0.01$). Under these experimental conditions, there were no significant effects on the other phases of the SCC response.

It was not possible to measure a SCC response at concentrations >10 μM because the cellular resistance of the monolayers decreased to <500 ohm $cm^2$. The initial rapid transient response was inhibited over the concentration range of 1 nM -1 μM.

Thus GI262570 decreased CFTR-mediated anion secretion in response to ADH stimulation in a cell culture model of the principal cells (MDCK-C7 cells).

The invention claimed is:

1. A method of treating autosomal dominant polycystic kidney disease in a human which comprises the administration of farglitazar or a pharmaceutically acceptable salt thereof to said human in need thereof.

* * * * *